Figure 1:
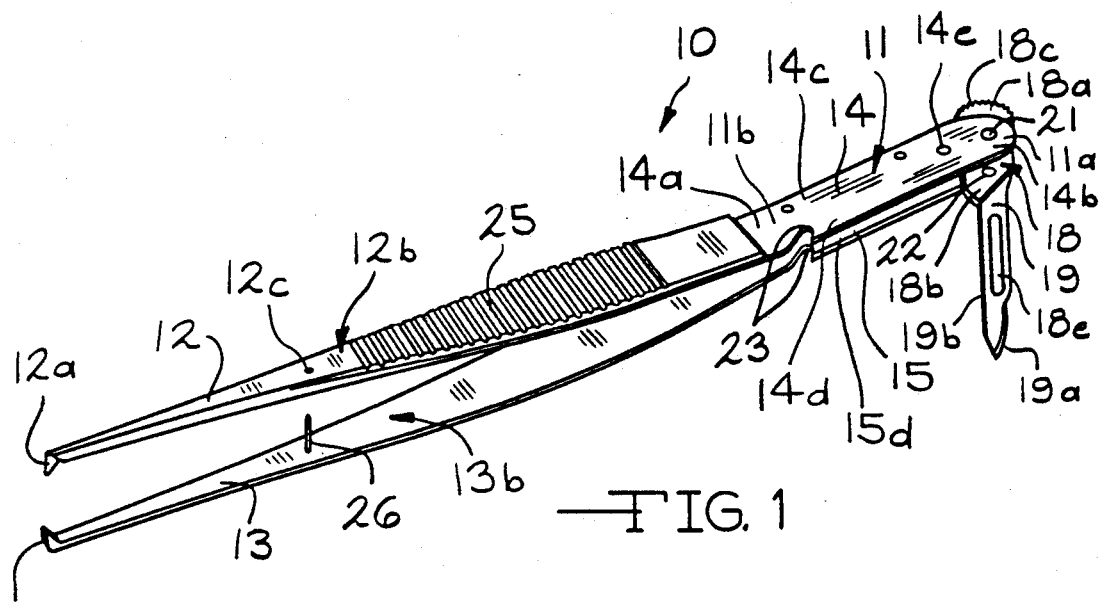

United States Patent [19]

Jones

[11] Patent Number: 5,015,252
[45] Date of Patent: May 14, 1991

[54] SURGICAL FORCEPS WITH SUTURE CUTTERS

[76] Inventor: Mark W. Jones, 841 Audubon St., East Lansing, Mich. 48823

[21] Appl. No.: 565,687
[22] Filed: Aug. 13, 1990
[51] Int. Cl.⁵ .................. A61B 17/28; A61B 17/32
[52] U.S. Cl. .................... 606/205; 606/167; 606/211; 7/118; 30/155
[58] Field of Search ............... 606/167, 174, 131, 148, 606/205, 206, 207, 210, 211; 30/155–161; 294/992; 7/118

[56] References Cited

U.S. PATENT DOCUMENTS

| | | |
|---|---|---|
| 219,633 | 9/1879 | Gifford . |
| 223,444 | 1/1880 | Gifford . |
| 574,178 | 12/1896 | Stebbins . |
| 1,046,361 | 12/1912 | Wulff . |
| 1,456,844 | 5/1923 | DiBie .................. 294/99.2 |
| 2,069,636 | 2/1937 | Wilson .................. 606/174 |
| 2,608,698 | 9/1952 | Mindheim . |
| 2,696,621 | 12/1954 | Miller .................. 7/118 |
| 2,998,649 | 9/1961 | Miller et al. . |
| 3,054,182 | 9/1962 | Whitton, Jr. . |
| 3,266,493 | 8/1966 | Cummings . |
| 3,364,572 | 1/1968 | Hoppe . |
| 3,576,072 | 4/1971 | Foster .................. 606/131 |
| 3,879,846 | 4/1975 | Allen, Jr. . |
| 4,053,979 | 10/1977 | Tuthill et al. . |
| 4,271,838 | 6/1981 | Lasner et al. . |

FOREIGN PATENT DOCUMENTS

| | | | |
|---|---|---|---|
| 2371912 | 6/1978 | France .................. 606/174 |
| 8300994 | 3/1983 | World Int. Prop. O. .......... 606/174 |

*Primary Examiner*—C. Fred Rosenbaum
*Assistant Examiner*—William W. Lewis
*Attorney, Agent, or Firm*—Ian C. McLeod

[57] ABSTRACT

An improved forceps device (10) is described. The forceps device includes a handle (11) formed of spaced apart plates (14) and (15) joined by bridge member (16) to form a pocket (17). Spaced apart arms (12) and (13) form the distal end of the handle and terminate at inwardly facing pointed ends (12a) and (13a) that are used to pull the sides of a surgical incision together so that the surgeon can close the incision with sutures. The handle provides for a holder (18) and a knife blade (19) that fold out of the pocket when the surgeon presses his or her thumb against a serrated protrusion (18c) that protrudes from the proximal end of the handle.

14 Claims, 1 Drawing Sheet

U.S. Patent

May 14, 1991

5,015,252

SURGICAL FORCEPS WITH SUTURE CUTTERS

BACKGROUND OF THE INVENTION (1) Field of the Invention

The present invention relates to a surgical forceps device with a suture cutter in the handle of the forceps. In particular, the present invention relates to a surgical forceps device with inward facing points at the end of spaced apart arms that are specifically designed to hold the sides of a surgical incision together during suturing. The handle of the forceps provides for a knife blade that is partially exposed by a notch in the handle so that a suture can be cut by pulling the suture against the knife blade. The knife blade preferably folds out of the handle for changing.

(2) Prior Art

The prior art has described various types of devices for cutting and removing sutures from a healed or closed incision. These devices are generally comprised of tweezers or forceps that are held between the thumb and forefinger. The devices enable a surgeon or nurse to pick a suture away from an incision and cut the suture. The prior art has also described combination tools used for plucking and cutting small objects other than sutures. Illustrative of the prior art suture cutters and combination tool devices are U.S. Pat. No. 219,633 to Gifford; 223,444 to Gifford; 574,178 to Stebbins; 1,046,361 to Wulff; 2,608,698 to Mindheim; 2,998,649 to Miller et al; 3,054,182 to Whitton, Jr.; 3,266,493 to Cummings; 3,364,572 to Hoppe; 3,879,846 to Allen, Jr.; 4,053,979 to Tuthill et al; 4,271,838 to Lasner et al.

Gifford describe two types of tweezer devices. One U.S. Pat. No. 223,444 describes a retractable knife between the arms of the tweezers while the other U.S. Pat. No. 219,633 describes a file and fingernail cutter When the knife is retracted it is not functional.

Stebbins describes cutting shears with a can opener at a distal end of one of the legs of the shears.

Wulff describes tweezers that are foldable into a pocket knife. The blade is not functional when folded into the knife.

Mindheim discloses a forceps-like tool with cutting blades in opposed legs of the forceps so that stubs, threads, thread ends, knots and other extraneous material in a piece of woven fabric can be picked out and cut away to leave the fabric in a smooth and finished condition.

Miller et al describes spaced apart legs in the form of tweezers that are equipped with a cutter which operates on a punch and die principle. One of the legs has a wedge with a notch while the other leg provides for a slot. The leg with the wedge is slid under the suture until the suture slips into the notch. The tweezers are then closed together and the suture is sheared when the wedge engages the leg with the slot.

Whitton, Jr. describes a device particularly adapted for lifting and cutting surgical sutures that is comprised of U-shaped tweezers having spaced apart elongated straight arms formed from an integral intermediate curved portion One of the arms forms a rounded probe for lifting sutures while the other arm comprises a blade in a holder that provides for traverse movement toward the lifted suture, thereby cutting the suture when the spaced apart arms are squeezed together.

Cummings combines scissors and tweezers in a single device. The scissors and tweezers are so related that a suture can be cut and removed in a continuous operation while the instrument is still held in the fingers of the operator. The device may be rotated by the fingers to position either the scissors or a gripping means in the proper position to effectually cut and remove sutures.

Hoppe describes a slender elongated device in the form of tweezers having narrow jaws at an outer or operating end for engaging and holding a suture. A knife is arranged to slide adjacent to the operating end of the device. A spring biased plunger near the grasping portion of the device is operable by the hand for causing the knife to slide forward and sever the suture close to the point where the suture is being engaged and held at the outer end of the device.

Allen, Jr. describes a combination device for cutting and removing surgical sutures that consists of tweezers with a longitudinal suture cutting element extending between spaced apart arms of the tweezers. The suture cutting element is anchored to one arm and to the bight of the tweezers body.

Tuthill et al describes a disposable suture cutter formed of tweezers that are held between the fingers and thumb. The tweezers have opposed free ends with one of the free ends shaped so that it can be inserted under a suture with a suture retaining groove for holding the suture. A cutting blade is attached to the other free end of the tweezers. The cutting blade end of the tweezers allows for movement traversely and downwardly to cut the suture being held by the retaining groove.

Lasner et al describes a forceps device for cutting sutures that is comprised of two shanks pivotably connected at a point intermediate their respective handle ends and their tool ends. The tool end of one of the shanks provides for a blade with a knife edge while the other tool end provides for a member that bifurcates into spaced apart arms that form a slot. The spaced apart arms allow for a suture to slide into the slot without the suture pulling through the slot when a knot is tied in the suture. When the handle ends are squeezed together, the blade shearingly contacts the spaced apart arms on the side of the member away from the closed incision so that when the physician snips the end of the suture, there is not a risk of also cutting living tissue. A variation of the device provides for shearing contact between the blade and the member in the form of tweezers.

The problem with the prior art is that the devices are either designed to only cut and remove sutures after the incision has been sutured closed, or they consist of tweezers that are not specifically designed for use in a surgical environment.

OBJECTS

It is therefore an object of the present invention to provide an improved forceps device that is specifically designed to help a surgeon pull the sides of an incision together for suturing and then cut the finished tied suture. Further, it is an object of the present invention to provide an improved forceps device with a knife blade positioned such that the device allows a surgeon to cut a suture without a risk of also cutting living tissue. Further, it is an object of the present invention to provide an improved forceps device with a knife blade that folds out of the forceps device for replacing the knife blade. Still further, it is an object of the present invention to provide an improved forceps device that is simple and inexpensive to manufacture and of a design that is easy to manipulate in a surgical environment. These and other objects will become increasingly apparent by reference to the following descriptions and to the drawings.

IN THE DRAWINGS

FIG. 1 is a right side perspective view of the forceps 10 particularly showing the handle 11, the moveable arms 12 and 13, the holder 18 and the knife blade 19 in its replacement position.

Figure 2:
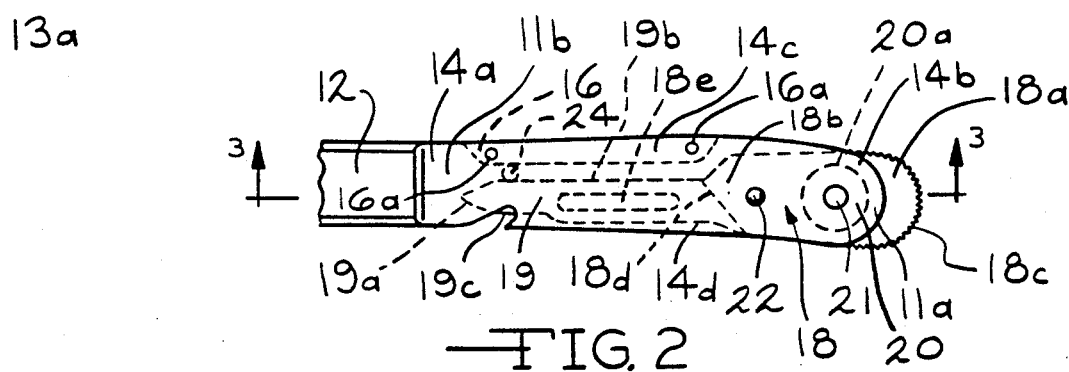

FIG. 2 is a plan perspective view of the holder 18 and the knife blade 19 folded into the handle 11 in its use position for insertion of a suture into notch 23 against cutting edge 19a of blade 19.

Figure 3:
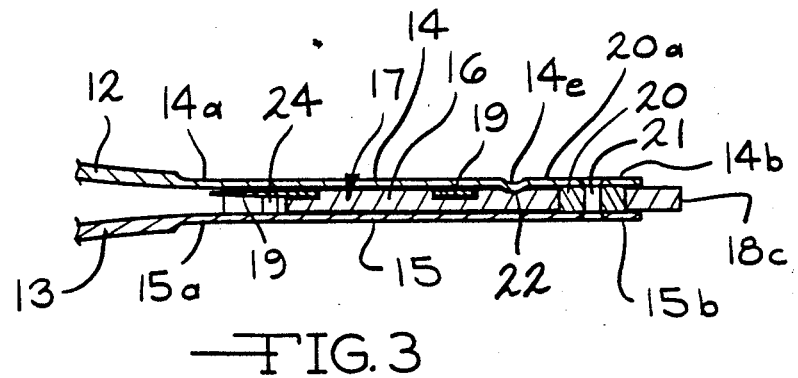

FIG. 3 is a cross-sectional view along line 3—3 of FIG. 2 showing the holder 18 and the knife blade 19 folded into the handle 11.

GENERAL DESCRIPTION

The present invention relates to a device for closing and suturing an incision in the skin of a living body which comprises: forceps having a proximal handle and distal spaced apart moveable arms attached to the handle for pulling the sides of the incision together; and a knife blade which is mounted within the handle, wherein a notch is provided in the handle adjacent the blade such that a suture can be inserted into the notch and cut by the blade after the suture is inserted in the incision without injuring a user of the device.

Further, the present invention relates to a device for closing and suturing an incision in the skin of a living body which comprises: forceps having a proximal handle and distal spaced apart moveable arms attached to the handle for pulling the sides of the incision together; and a knife blade which is foldable into and out of the handle, wherein a notch is provided in the handle adjacent the folded blade such that a suture can be inserted into the notch and cut by the blade after the suture is inserted in the incision without injuring a user of the device.

The present invention relates to a device for closing and suturing an incision in the skin of a living body which comprises: forceps having a proximal handle and distal spaced apart moveable arms attached to the handle for pulling the sides of the incision together; and a knife blade which is foldable into and out of the handle, wherein a notch is provided in the handle adjacent the folded blade such that a suture can be inserted into the notch and cut by the blade after the suture is inserted in the incision without injuring a user of the device.

The forceps device is preferably constructed of a spring material such as stainless steel that will provide for the arms of the forceps to be spaced apart when the forceps are in the rest position. The spring material exerts a restraining force against the surgeon's thumb and forefinger that helps the surgeon control the forceps when the surgeon pulls the sides of an incision together for suturing. The disposable knife blade is preferably a sterile surgeon's blade, size 15, and is replaced after each use. It is possible for the improved forceps and blade to be sterilized; however, normally the blade is replaced after suturing a wound and sterilizing the forceps.

SPECIFIC DESCRIPTION

FIGS. 1 to 3 show a forceps device 10 of the present invention which comprises a handle 11 and spaced apart moveable arms 12 and 13, and a foldable holder 18 mounting a knife blade 19. The handle 11 is generally rectangular in cross-section and comprises spaced apart plates 14 and 15 and bridge member 16. Plate 14 has spaced apart ends 14a and 14b, and sides 14c and 14d between the ends 14a and 14b. Similarly, plate 15 has spaced apart ends 15a and 15b, and sides (only 15d shown) between the ends 15a and 15b. The plates 14 and 15 are joined at the back sides (only 14c shown) by a bridge member 16 with rivets 16a through the plates 14 and 15 thereby forming pocket 17 (FIG. 3) for housing the holder 18 with knife blade 19 in handle 11. The knife blade 19 has a knife edge 19a and is preferably a disposable surgeon's blade.

The holder 18 has a proximal end 18a and a distal end 18b with an intermediate pivot ring 20 that is machine fit into opening 20a (FIG. 2). The holder 18 and pivot ring 20 pivot between a folded position wherein the knife blade 19 and holder 18 are concealed in pocket 17, and an unfolded position wherein the knife blade 19 is moved out of the pocket 17 by arcuate movement of the holder 18 and pivot ring 20 around a pivot pin 21. The proximal end 18a of the holder 18 has a serrated protrusion 18c that protrudes from the proximal end 11a of the handle 11. To change the knife blade 19, a surgeon presses the serrated protrusion 18c with his or her thumb which causes the holder 18 and knife blade 19 to pivot out of pocket 17 on pivot pin 21. The surgeon then lifts up and pulls the knife blade 19 out of a retaining slot 18d in holder 18 from pin 18e as is conventional for surgical knives. The old knife blade 19 can then be discarded and replaced with a new one.

An inwardly protruding retaining indentation 14e is provided in plate 14 and mates with a spherical recess 22 provided in holder 18 adjacent to pivot pin 21 (FIG. 3). The indentation 14e and the spherical recess 22 act as a locking means that helps to retain the holder 18 and knife blade 19 in the pocket 17 when the knife blade 19 is in the use position. A U-shaped notch 23 that angles away from the proximal end 11a of the handle 11 is provided in sides 14d and 15d of the plates 14 and 15 adjacent to the distal end 18b of holder 18 for receiving a suture to be cut. A stop pin 24 is provided between plates 14 and 15 adjacent to the notch 23 so that when the knife blade 19 is in the folded position, the back side 19b of the knife blade 19 rests against the stop pin 24 while the knife edge 19a is adjacent to notch 23. Alternatively, the blade 19 could rest on bridge member 16 and the stop pin 24 could be eliminated (not shown). In the folded position, the majority of the knife edge 19a is concealed in pocket 17 with a portion 19c of the knife blade 19 protruding out from the notch 23. This allows a suture to be pulled into notch 23 against knife edge 19a and cut without unfolding the knife blade 19 from the handle 11.

Spaced apart arms 12 and 13 extend from the ends 14a and 14b of plates 14 and 15 at the distal end 11b of handle 11. The arms 12 and 13 terminate at inward facing pointed ends 12a and 13a which are angled toward each other for pinching the sides of a surgical incision together for suturing. The upper surface 12b of the arm 12 and the lower surface of arm 13 (not shown) have serrations 25 that helps in gripping the forceps 10. Between the serrations 25 and the pointed ends 12a and 13a, an opening 12c is provided through arm 12 and a guide pin 26 is mounted in the inside wall 13b of arm 13 for mating with opening 12c. When the arms 12 and 13 are squeezed together, the pointed ends 12a and 13a contact each other. This provides precise registering of the pointed ends 12a and 13a. However, the arms 12 and 13 are prevented from moving too close together by opening 12c which provides for mating with guide pin 26 but which does not allow guide pin 26 to pass through the opening 12c.

In use of the forceps 10, the surgeon pulls the wound together with ends 12a and 13a of arms 12 and 13. The suture (not shown) is inserted in the incision and tied. The forceps are then turned around and the suture inserted in notch 23 and cut by blade 19 at 19c. The result is rapid and reliable suturing of an incision.

It is intended that the foregoing description be only illustrative of the present invention and that the present invention be limited only by the hereinafter appended claims.

I claim:

1. A device for closing and suturing an incision in the skin of a living body which comprises:
   (a) forceps having a proximal handle and distal spaced apart moveable arms attached to the handle for pulling the sides of the incision together; and
   (b) a knife blade which is mounted within the handle, wherein a notch is provided in the handle adjacent the blade such that a suture can be inserted into the notch and cut by the blade after the suture is inserted in the incision without injuring a user of the device.

2. The device of claim 1 wherein the arms are biased apart and can be pressed together to close the incision.

3. The device of claim 2 wherein the arms are made of a spring material which acts to hold the arms apart.

4. The device of claim 1 wherein the notch is angled towards the proximal end of the device.

5. A device for closing and suturing an incision in the skin of a living body which comprises:
   (a) forceps having a proximal handle and distal spaced apart moveable arms attached to the handle for pulling the sides of the incision together; and
   (b) a knife blade which is foldable into and out of the handle, wherein a notch is provided in the handle adjacent the folded blade such that a suture can be inserted into the notch and cut by the blade after the suture is inserted in the incision without injuring a user of the device.

6. The device of claim 5 wherein the blade is removeable from a holder which folds into the handle.

7. The device of claim 5 wherein the arms are biased apart and can be pressed together to close the incision.

8. The device of claim 7 wherein the arms are made of a spring material which acts to hold the arms apart.

9. The device of claim 5 wherein the notch is angled towards the proximal end of the device.

10. A method for suturing an incision in the skin of a living body which comprises:
    (a) providing forceps having a proximal handle and distal spaced apart moveable arms attached to the handle for pulling the sides of the incision together and a knife blade mounted within the handle, wherein a notch is provided in the handle adjacent the blade such that a suture can be inserted into the notch and cut by the blade after the suture is inserted in the incision without injuring a user of the device; and
    (b) using the arms of the device to pull the sides of the incision together so that the incision can be sutured closed; and
    (c) cutting the suture outside of the incision with the blade by inserting the suture into the notch and pulling the suture against the blade until the suture cuts.

11. The method of claim 10 wherein the blade is removeable from a holder which folds into the handle and wherein after suturing of the wound the blade is removed from the holder and discarded.

12. The method of claim 10 wherein the arms are biased apart and can be pressed together to close the incision.

13. The method of claim 12 wherein the arms are made of a spring material which acts to hold the arms apart.

14. The method of claim 10 wherein the notch is angled towards the distal end of the device and wherein the handle is directed towards the incision and adjacent to the suture and the suture is then cut.

* * * * *